(12) United States Patent
Jovancicevic et al.

(10) Patent No.: US 8,109,161 B2
(45) Date of Patent: Feb. 7, 2012

(54) METHODS AND APPARATUS FOR MONITORING DEPOSIT FORMATION IN GAS SYSTEMS

(75) Inventors: Vladimir Jovancicevic, Richmond, TX (US); Sunder Ramachandran, Sugar Land, TX (US); Paul Hammonds, Dubai (AE)

(73) Assignee: Baker Hughes Incorporated, Houston, TX (US)

( * ) Notice: Subject to any disclaimer, the term of this patent is extended or adjusted under 35 U.S.C. 154(b) by 498 days.

(21) Appl. No.: 12/393,202

(22) Filed: Feb. 26, 2009

(65) Prior Publication Data
US 2009/0211335 A1 Aug. 27, 2009

Related U.S. Application Data

(60) Provisional application No. 61/031,740, filed on Feb. 27, 2008.

(51) Int. Cl.
*G01M 19/00* (2006.01)
(52) U.S. Cl. ....................................................... 73/865.8
(58) Field of Classification Search .................. None
See application file for complete search history.

(56) References Cited

U.S. PATENT DOCUMENTS

| | | | |
|---|---|---|---|
| 2,404,474 A | 7/1946 | Collins | |
| 4,561,286 A * | 12/1985 | Sekler et al. | 73/24.06 |
| 5,201,215 A | 4/1993 | Granstaff et al. | |
| 5,208,162 A | 5/1993 | Osborne et al. | |
| 5,661,233 A | 8/1997 | Spates et al. | |
| 5,734,098 A | 3/1998 | Kraus et al. | |
| 6,125,687 A * | 10/2000 | McClelland et al. | 73/19.01 |
| 6,141,625 A * | 10/2000 | Smith et al. | 702/50 |
| 6,156,578 A * | 12/2000 | Tom | 436/149 |
| 6,323,442 B1 | 11/2001 | Jones | |
| 6,499,876 B1 | 12/2002 | Baginksi et al. | |
| 6,886,393 B1 | 5/2005 | Romanet et al. | |
| 6,942,782 B2 * | 9/2005 | Shevchenko et al. | 205/793.5 |
| 6,959,588 B2 | 11/2005 | Zougari et al. | |
| 2002/0189868 A1 * | 12/2002 | Cain et al. | 177/210 FP |
| 2006/0260385 A1 * | 11/2006 | Galun et al. | 73/24.04 |
| 2007/0187646 A1 | 8/2007 | Fellers | |

FOREIGN PATENT DOCUMENTS

WO 2006054076 A1 5/2006

OTHER PUBLICATIONS

J. S. Smart, et al., "Pigging and Chemical Treatment of Pipelines," The Pipeline Pigging Conference, Feb. 2-5, 1998, Houston, Texas.

(Continued)

*Primary Examiner* — Robert R Raevis
(74) *Attorney, Agent, or Firm* — Mossman Kumar & Tyler PC

(57) ABSTRACT

Solids deposition in a gas environment, such as a gas transmission line or pipeline are measured using metal-coated quartz crystal microbalance (QCM) in a QCM probe within a high pressure gas chamber in the gas environment. The metal coated on the QCM may be iron, iron alloys and/or iron oxide. The weight measurements are conducted at a constant ($\Delta T$) or controlled ($T=f(t)$) temperature between the high pressure gas chamber and the QCM probe. The weight gain during a CE cycle is associated with the solids formation rate.

18 Claims, 2 Drawing Sheets

OTHER PUBLICATIONS

"Movement of Black Powder in Gas Pipelines," Pipeline & Gas Journal, article excerpt, Oct. 1, 2007, available from: http://goliath.ecnext.com/coms2/gi_0199-7196130/Movement-of-black-powder-in.html.

"Black Powder in Gas Pipelines", Wikipedia, Mar. 2008, available from: http://en.wikipedia.org/wiki/Black_powder_in_gas_pipelines.

* cited by examiner

METHODS AND APPARATUS FOR MONITORING DEPOSIT FORMATION IN GAS SYSTEMS

CROSS-REFERENCE TO RELATED APPLICATION

This application claims the benefit of U.S. Provisional Patent Application 61/031,740 filed Feb. 27, 2008.

TECHNICAL FIELD

The invention relates to methods and apparatus for measuring solids deposits in a gas environment, and most particularly relates, in one non-limiting embodiment, to methods and apparatus for measuring the formation of "black powder" in gas transmission lines.

TECHNICAL BACKGROUND

"Black powder" formation in gas transmission lines, such as sales gas lines, is a problem that has had a serious impact on pipeline operations including, but not necessarily limited to, erosion failures of valves, lower efficiency of compressors, clogging of instrumentation and valves, and problems with Health, Safety & Environment (HS&E) compliance. Despite the fact that this has been a persistent problem in the industry, there has been little work towards ascertaining the composition, sources and formation mechanism of black powder in gas transmission lines. Acquiring such knowledge through the development of methodology for measuring the rate of black powder formation is critical for the development of effective strategies to predict and control black powder formation.

"Black powder" is a color descriptive term used loosely to describe blackish material that collects in gas pipelines. It has a "wet" tar-like appearance, or may appear as a "dry" fine powder material that is mainly composed of iron hydroxide, iron carbonate and iron sulfide mixed with various contaminants such as salts, sand and liquid hydrocarbons. J. Smart in "Movement of Black Powder in Gas Pipelines", *Pipeline and Gas Journal*, Oct. 1, 2007, notes that black powder is a catch-all term for solids in a gas pipeline, ranging from 100% iron sulfide to 100% iron oxide, also containing rouge, asphaltenes, salt, sand, clay, weld spatter and metallic iron.

In one non-limiting explanation, black powder is believed to be generated during gas production or in gas pipelines when hydrogen sulfide, carbon dioxide or oxygen are present in the gas, by bacterial corrosion of the steel, or from construction when lines are not cleaned adequately. Black powder is even known to exist in new pipelines. In one non-limiting theory of black powder development, water is involved in its formation.

Once in a pipeline, black powder is transported through the pipeline by gas flow. The velocity required to move dry solids in a pipeline can be calculated and depends on pipeline diameter, gas pressure, particle size and particle density. Typical velocities required at 1,000 psi (6.9 MPa) may be 10 ft/sec (3 m/sec) for 8-inch (20 cm) lines, 13 ft/sec (4 m/s) in 24-inch (61 cm) lines and 14 ft/sec (4.3 m/s) in 48-inch (122 cm) lines. Black powder may be a significant operating parameter in wet and dry gas pipelines. Operators report that when black powder moves, it shatters and becomes very small in size, in the range of one micron or less, making it difficult to filter and possibly easier to move.

Deposition of black powder will occur if there are solids in the pipeline fluid and the velocity is not high enough to drag the particles along by viscous flow forces. Sediment deposits can lead to blockage of the line, especially during pigging, while flowing powder can damage compressors, plug filters and damage user equipment. One operator reported that when piping upstream of a compressor was inspected, the piping was half full of black powder, causing shutdown of the compressor and that 60 tons of black powder were subsequently removed from the piping. Black powder also represents a threat to natural gas's reputation as a clean fuel.

It would be desirable if a new methodology for measuring black powder formation rate under field conditions that would allow for the improvements of the current technologies for preventing black powder formation in gas transmission lines could be developed.

SUMMARY

There is provided, in one non-limiting form, a method of measuring solids deposits, such as black powder, in a gas environment, such as a high pressure gas test chamber, a gas transmission line or pipeline. The method involves initially measuring the weight gain due to water condensation on a metal-coated quartz crystal microbalance (QCM) in a QCM probe within a high pressure gas chamber of the gas environment. The QCM probe is cooled during the condensation period at constant $\Delta T$ (constant condensation rate) or at a controlled $\Delta T$ (constant condensation layer) ($\Delta T = f(t)$).

As the probe is cooled, the rate of change of weight is associated with both the condensation rate and the metal oxidation rate. Subsequently, the probe is heated to the temperature of the gas during the evaporation period of the condensation evaporation (CE) cycle. The final solids deposits weight gain is determined during each CE cycle. The solids deposits weight gain of the metal-coated QCM is continuously measured during at least one subsequent CE cycle, but in most cases during multiple CE cycles. A cumulative solids deposits rate is determined. The weight measurements are conducted at temperature differentials ($\Delta T$) between the high pressure gas chamber and the QCM probe.

In one non-limiting embodiment, there is provided an apparatus for measuring solids deposits in a gas environment that includes a temperature-controlled high pressure gas chamber, a gas mixing and delivery system adapted to mix gases and deliver them to the high pressure gas chamber at certain temperatures at or above atmospheric, a temperature-controlled quartz crystal microbalance (QCM) probe that includes a temperature-controlled metal-coated QCM within a high pressure gas chamber in the gas environment, a frequency generator and data acquisition system. The system is adapted to acquire measurements including, but not necessarily limited to, a solids deposits weight gain on the temperature-controlled metal-coated QCM, a dew point, a condensation rate during a condensation-evaporation (CE) cycle, a cumulative solids deposits rate, and combinations thereof. The apparatus also includes a gas chromatograph. The gas chromatograph measures gas composition before and after the CE measurement cycle for any changes in gas composition. The temperature-controlled high pressure gas system and the temperature-controlled QCM probe are designed to maintain a constant temperature differential ($\Delta T$) between them.

It will be appreciated that the Figures are schematic illustrations that are not to scale and that certain features may be exaggerated for emphasis and that certain other features which are conventional may be omitted.

DETAILED DESCRIPTION

A new method and apparatus for measuring black powder formation rates in dry gas transmission lines as a function of various contaminants (e.g. $CO_2$, $O_2$, $H_2S$, water) has been discovered. The method is based on the continuous measurement of weight changes of a metal (e.g. mild steel) coated quartz crystal microbalance (QCM) during condensation-evaporation (CE) cycles in a dry gas environment. In addition to the measurement of the weight gain at the end of the CE cycle due to metal oxidation, the dew point and condensation rate are determined. The method includes determining the deposit (i.e. black powder) formation rate for various gas compositions and would allow for prediction of black powder formation and its control in gas transmission systems. Black powder control would include prevention of its formation initially, treatment of its existence to prevent more forming or remove the black powder present, and combinations of these.

A key feature of the proposed QCM method consists of conducting the weight measurements at constant temperature differential ($\Delta T$) between a high pressure test cell and the QCM probe during condensation and evaporation cycle. The method includes the steps of:
 (a) initial measurement of the weight change of metal coated quartz crystal microbalance due to water condensation (i.e. dew point);
 (b) subsequent measurement of the condensation rate and metal oxidation rate during condensation-evaporation cycle;
 (c) final measurement of weight change of the coated QCM after water evaporation of the CE cycle (i.e. black powder formation rate);
 (d) determination of the final weight change during each CE cycle; and
 (e) continuous measurements of weight change during subsequent CE cycles and determination of the cumulative black powder formation rates.

At the end of each CE cycle the following data are obtained:
 Final measurement of the weight gain on the QCM for that CE cycle and cumulative weight gain over certain time period;
 Dew point for that CE cycle and dew point as a function of time; and/or
 Gas composition for that CE cycle and gas compositions as a function of time.

The cumulative black powder formation rate may be measured at various locations in the QCM cell (e.g. top, bottom), along with $\Delta T$ and gas composition to gain a more complete understanding of black powder formation.

The effect of each contaminant in the gas phase on the black powder formation rate will be determined and quantitative relationships established. This will allow the development of a prediction model for black powder formation in gas transmission lines.

Figure 1:
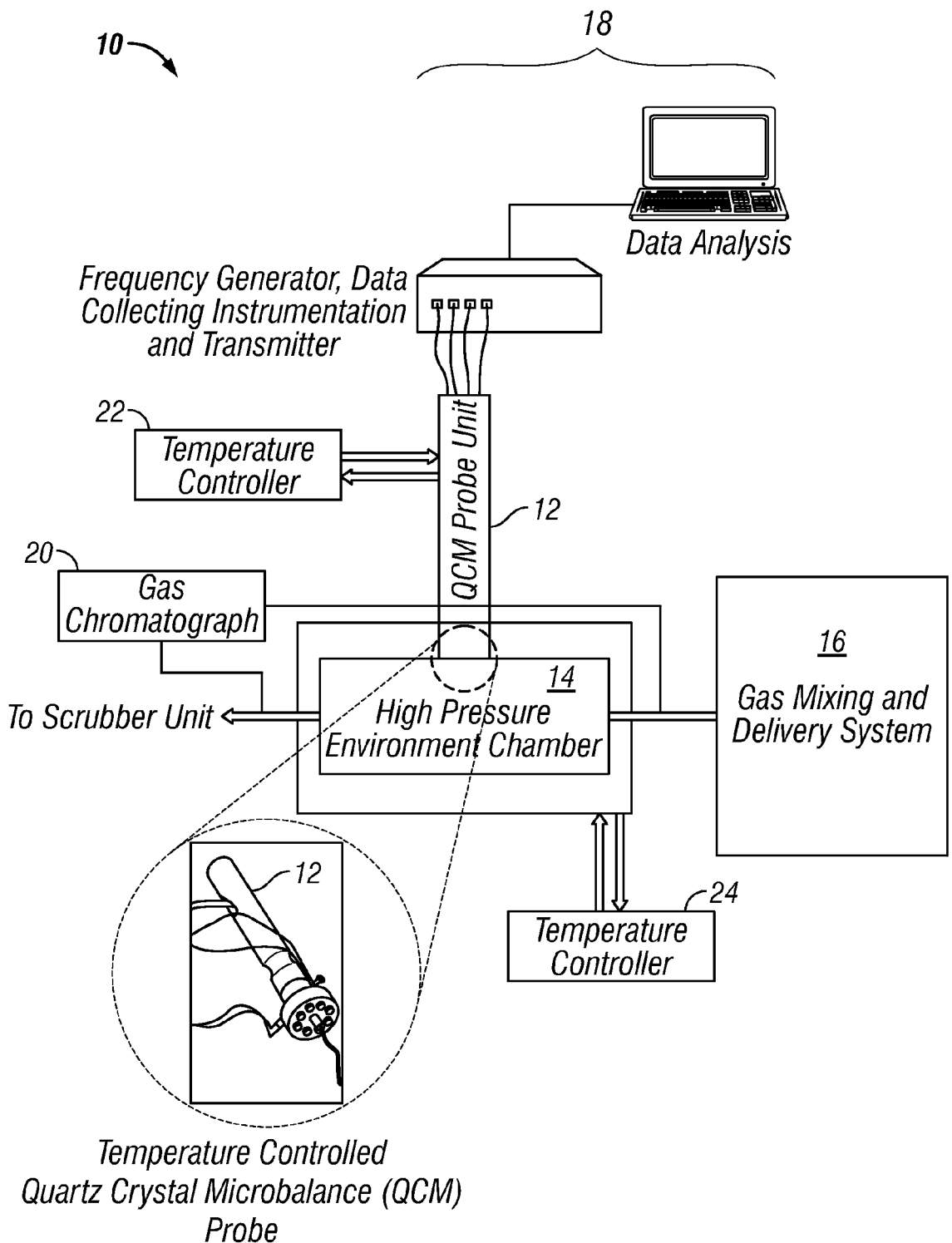
FIG. 1 is a schematic illustration of an experimental setup for measuring black powder formation rates in a gas.

A specially designed test apparatus 10 with a proprietary QCM probe 12 will be used to carry out the weight change measurements under the high pressure and constant condensation rate (constant $\Delta T$) or constant condensation layer (controlled $\Delta T$) conditions as shown in FIG. 1. The experimental setup includes:
 (i) a temperature controlled high pressure gas chamber 14,
 (ii) a gas mixing and delivery system 16,
 (iii) a temperature controlled QCM probe 12,
 (iv) a frequency generator and data acquisition system 18, and
 (v) a gas chromatograph 20 for chemically analyzing the gas composition of the high pressure gas chamber.

The temperature controlled QCM probe 12 will allow measurements of small weight changes to be made at either constant condensation rate (increasing film thickness) or constant water film thickness. The effects of condensed water and gas composition on black powder formation will be studied using wide concentration ranges for $H_2S$, $CO_2$ and $O_2$. One non-limiting concentration range for gas contaminants in a natural gas stream to be studied is given in Table 1. Gas temperatures may vary between about 0 and about 30° C. and the pressure may vary from about 700 to about 1000 psi (about 4.8 to about 6.9 MPa).

TABLE 1

| Gas Composition and Concentration Range of Sales Gas | |
|---|---|
| Gas Composition | Concentration Range |
| $H_2S$ | 2-6 ppm |
| $CO_2$ | 0.1-1.6% |
| $O_2$ | 0.01-0.05% |
| $H_2O$ in gas | 0.12-0.55 mg/L |

It is important for the temperature difference between the QCM probe 12 high pressure gas chamber 14 to be a constant, or controlled value. This may be accomplished by using first temperature controller 22 on the QCM probe 12 and second temperature controller 24 on the high pressure gas chamber 14.

Figure 2:
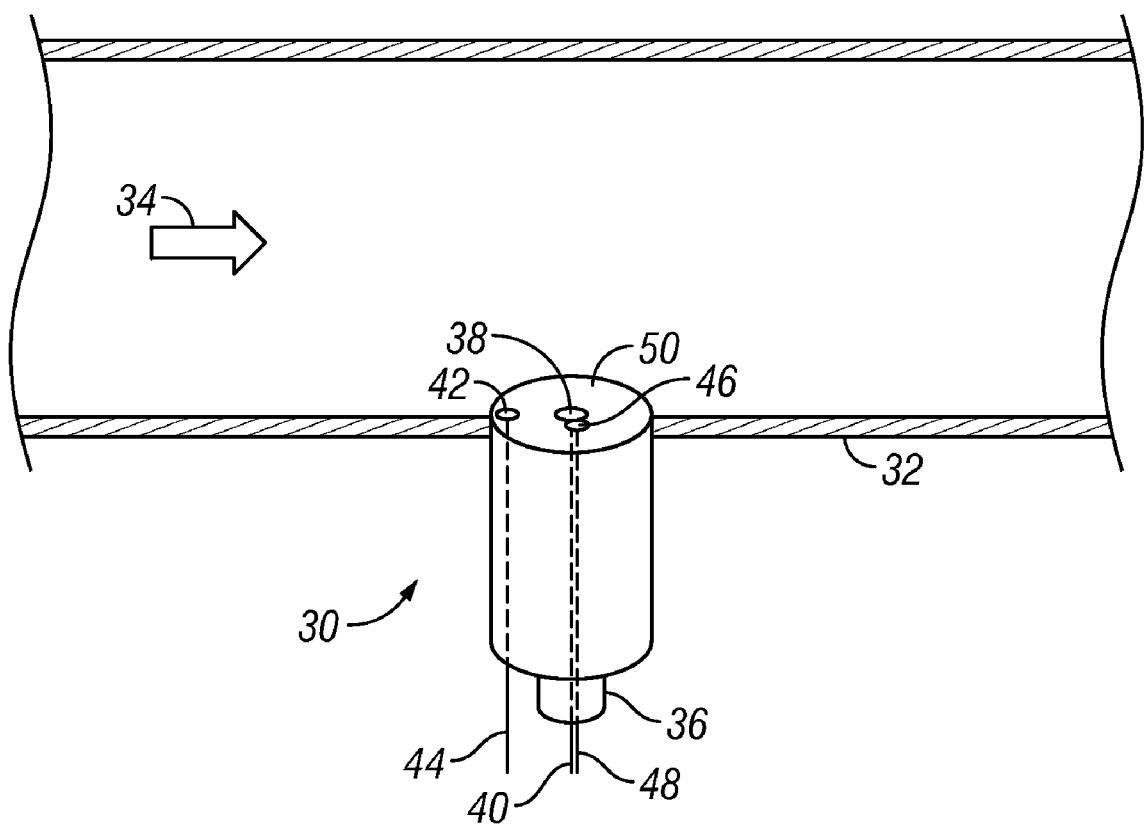
FIG. 2 is a schematic illustration of a QCM probe flush mounted in a pipe.

Shown in FIG. 2, is a schematic illustration of a deposition field QCM probe 30 flush mounted in a pipe 32 (shown in cross-section) where the fluid flow in the pipe 32 is in the direction of arrow 34 (left to right as oriented in FIG. 2). The field QCM probe 30 includes a temperature controlled, e.g. chilled or cooled, "finger" or rod 36 within probe 30 having the QCM 38 mounted on the end thereof. The finger or rod 36 may be chilled by any known or convenient chiller or mechanism, including, but not limited to, a refrigeration unit. The chilled finger, tip or rod 36 is mounted on end and exposed to the fluid in pipe 32. QCM 38 having connecting wire 40. QCM probe 30 also has two temperature measuring devices, (e.g. thermocouples), upstream fluid thermocouple 42 (having connecting wire 44) and QCM thermocouple 46 (having connecting wire 48), both on the end or tip of probe 30. Upstream fluid thermocouple 42 is adapted to sense fluid or gas temperature upstream of the QCM 38 to avoid reading cooled fluids; upstream fluid thermocouple 42 and QCM thermocouple 46 being on the end or tip 50 of probe 30. Upstream fluid thermocouple 42 is spaced apart from the QCM 38 since it is to sense the fluid or gas temperature, rather than the QCM 38 temperature. QCM thermocouple 46 is adapted to sense the QCM 38 surface temperature; the QCM thermocouple 46 is at least adjacent to if not touching QCM 38.

Quartz crystal microbalances are well known in the art. These devices measure a mass per unit area by measuring the change in the frequency of a quartz crystal resonator. The resonance is disturbed by the addition (or removal) of a small mass due to oxide growth (or decay) or film deposition on the surface of the acoustic resonator. However, QCMs are not known to be used to study or evaluate black powder formation rate. In the present method and apparatus, the QCMs are used only to study weight gain.

QCMs are known to study corrosive effects, as described in U.S. Pat. No. 5,208,162, incorporated by reference herein in its entirety. In the methods and apparatus therein, a QCM is coated with a corrodible metallic substance and has a known vibrational frequency. The QCM is excited in a corrosive atmosphere, and the change in the frequency of the vibration resulting from corrosion of the corrodible substance is measured during each of a plurality of intervals of time, including a reference interval and at least one subsequent measurement interval. This generates a thickness signal representing the thickness of corrosion corresponding to the measured change in frequency during the measurement interval. The corrosion thickness signal for the measurement interval is converted to a reference signal representing the thickness of corrosion accumulated during the reference interval. In the U.S. Pat. No. 5,208,162, the coated QCMs are disclosed to monitor corrosion in such environments as industrial process measurement and control rooms, motor control centers, electrical rooms, semiconductor clean rooms, electronic fabrication sites, commercial data centers, museums, libraries, and archival storage rooms.

In the present methods and apparatus, the metal coated on the QCM includes, but is not necessarily limited to, iron, iron alloys, iron oxide, and combinations thereof. The iron alloys would be similar or identical to the iron alloys most prevalent in the gas transmission line or other system being studied.

The metal is coated on the QCM by a method including, but not necessarily limited to thin film deposition, vacuum deposition, chemical vapor deposition (CVD), electroless plating, chemical solution deposition, physical vapor deposition, sputtering, pulsed laser deposition, cathodic arc deposition, reactive sputtering, molecular beam epitaxy, topotaxy, and combinations thereof. In one non-limiting embodiment, the vacuum deposition is physical vapor deposition (PVD) and is a general term used to describe any of a variety of methods to deposit thin films by the condensation of a vaporized form of the material onto the QCM surfaces. The PVD coating method involves purely physical processes such as high temperature vacuum evaporation or plasma sputter bombardment rather than an involving a chemical reaction at the surface to be coated as in CVD.

In one non-limiting embodiment, the cumulative black powder formation rate measured at various locations and temperature variations ($\Delta T$) along a given pipeline will allow for better prediction, prevention and control of black powder formation in that pipeline. Multiple locations for data collection will also help further identify the critical locations and conditions for the black powder formation in gas pipelines and thus its prevention at those locations. Current methods employed in the industry are mainly concerned with removal and dissolution of the deposited black powder, for instance the use of chemical cleaners and pigging, rather than its inhibition and control as in the present method and apparatus.

The invention will now be described with respect to an Example which is not intended to limit the method or apparatus of the invention in any way, but to simply illuminate a non-limiting embodiment thereof.

Example 1

A QCM probe coated with thin film of iron would be placed in a temperature-controlled high pressure gas chamber and maintained at a constant temperature (which would be lower than temperature of the gas chamber) for induced water condensation (condensation cycle). The condensed water would result in an increase in weight of the QCM probe. The condensed water on the iron-coated QCM probe with absorbed gases ($CO_2$, $H_2S$, $O_2$) would cause the iron to corrode leading to further weight gain of the QCM. After subsequent increase in temperature of the QCM probe the water layer would evaporate (evaporation cycle) resulting in a net weight gain due to black powder formed during the condensation cycle. In these experiments, the temperature of the gas chamber would be varied between 5 and 50° C. while pressure would be maintained between 15 and 1000 psi (0.1 to 6.9 MPa). The temperature differential between the QCM and the gas chamber would be in the range from 0 to 50° C.

Many modifications may be made in the methods of and apparatus of this invention without departing from the spirit and scope thereof that are defined only in the appended claims. For example, the exact methods and steps therein and apparatus may be different from those explicitly mentioned or suggested here. Additionally, techniques and methods for measuring the various parameters other than those specifically mentioned may find utility in the methods of this invention. Various combinations of QCMs, and other measuring devices and measuring processes besides those explicitly mentioned herein are expected to be useful.

The present invention may suitably comprise, consist or consist essentially of the elements disclosed and may be practiced in the absence of an element not disclosed.

The words "comprising" and "comprises" as used herein throughout the claims, are to be interpreted as "including but not limited to" and "includes but not limited to".

What is claimed is:
1. A method of measuring solids deposits in a gas environment comprising:
   initially measuring the weight gain due to water condensation on a metal-coated quartz crystal microbalance (QCM) in a QCM probe within a high pressure gas chamber of the gas environment;
   subsequent to the initial measuring, measuring the condensation rate and the metal oxidation rate during a condensation period of the condensation-evaporation (CE) cycle;
   finally measuring the solids deposits weight gain of the metal-coated QCM after water evaporation of the CE cycle;
   determining the final solids deposits weight gain during each CE cycle;
   continuously measuring the solids deposits weight gain of the metal-coated QCM during at least one subsequent CE cycle; and
   determining a cumulative solids deposits rate;
where the weight measurements are conducted at a condition selected from the group consisting of:
   constant ($\Delta T$) and
   a controlled variable temperature differential ($\Delta T = f(t)$) between the high pressure gas chamber and the QCM probe.
2. The method of claim 1 where the gas environment is a gas transmission line.
3. The method of claim 1 where the metal coated on the QCM is selected from the group consisting of iron, iron alloys, iron oxide, and combinations thereof.
4. The method of claim 1 where the solids deposits are black powder.

5. The method of claim 1 where a solids deposits weight gain is measured at more than one point in the high pressure gas chamber.

6. The method of claim 1 further comprising heating the probe to the temperature of the gas during water evaporation of the CE cycle.

7. A method of measuring black powder deposits in a gas transmission line comprising:
   initially measuring the weight gain due to water condensation on a metal-coated quartz crystal microbalance (QCM) in a QCM probe within a high pressure gas chamber of the gas transmission line;
   subsequent to the initial measuring, measuring the condensation rate and the metal oxidation rate during a condensation period of the condensation-evaporation (CE) cycle;
   finally measuring the black powder deposits weight gain of the metal-coated QCM after water evaporation of the CE cycle;
   determining the final black powder deposits weight gain during each CE cycle;
   continuously measuring the black powder deposits weight gain of the metal-coated QCM during at least one subsequent CE cycle; and
   determining a cumulative black powder deposits rate;
   where the weight measurements are conducted at a condition selected from the group consisting of:
   constant ($\Delta T$) and
   a controlled variable temperature differential ($\Delta T=f(t)$) between the high pressure gas chamber and the QCM probe.

8. The method of claim 7 where the metal coated on the QCM is selected from the group consisting of iron, iron alloys, iron oxide, and combinations thereof.

9. The method of claim 7 where a solids deposits weight gain is measured at more than one point in the high pressure gas chamber.

10. The method of claim 7 further comprising heating the probe to the temperature of the gas during water evaporation of the CE cycle.

11. An apparatus for measuring solids deposits in a gas environment comprising:
    a temperature-controlled high pressure gas chamber in the gas environment;
    a gas mixing and delivery system adapted to mix gases and deliver them to the high pressure gas chamber at temperatures at or above atmospheric;
    a temperature-controlled quartz crystal microbalance (QCM) probe comprising a temperature-controlled metal-coated QCM within the high pressure gas chamber in the gas environment;
    a frequency generator and data acquisition system adapted to acquire measurements comprising a solids deposits weight gain on the temperature-controlled metal-coated QCM, a dew point, a condensation rate during a condensation-evaporation (CE) cycle, a cumulative solids deposits rate, and combinations thereof; and
    a gas chromatograph adapted to chemically analyze the gas composition of the temperature-controlled high pressure gas chamber.

12. The apparatus of claim 11 where the gas environment is a gas transmission line.

13. The apparatus of claim 12 where the gas transmission line contains a plurality of QCM probes.

14. The apparatus of claim 11 where the metal coated on the QCM is selected from the group consisting of iron, iron alloys, iron oxide, and combinations thereof.

15. The apparatus of claim 11 where the solids deposits are black powder.

16. A field probe for measuring black powder deposits, the field probe comprising:
    a probe body having a tip;
    a metal-coated quartz crystal microbalance (QCM) on the tip of the probe;
    a QCM temperature measuring device on the tip of the probe, the QCM temperature measuring device at least adjacent to the QCM;
    an upstream fluid temperature measuring device on the tip of the probe, the upstream temperature measuring device spaced apart from the QCM; and
    a chiller for lowering the temperature of the QCM.

17. The field probe of claim 16 where at least one of the temperature measuring devices is a thermocouple.

18. The apparatus of claim 16 where the metal-coated QCM is coated with a metal selected from the group consisting of iron, iron alloys, iron oxide, and combinations thereof.

* * * * *